United States Patent [19]

Newton

[11] 4,284,496
[45] Aug. 18, 1981

[54] PARTICLE GUIDING APPARATUS AND METHOD

[76] Inventor: William A. Newton, Suite 238, 300 East Bldg., 300 31st St., North, St. Petersburg, Fla. 33713

[21] Appl. No.: 101,758

[22] Filed: Dec. 10, 1979

[51] Int. Cl.$^3$ .................................................. B07C 9/00

[52] U.S. Cl. .................................... 209/3.3; 209/44.1; 209/127 R; 324/71 CP; 356/72

[58] Field of Search ............................. 209/3, 3.1–3.3, 209/44.1, 127 R, 127 A, 127 B, 127 C, 128–130, 576, 577, 579; 324/71 CP; 356/72, 335, 336

[56] References Cited

U.S. PATENT DOCUMENTS

| | | | |
|---|---|---|---|
| 2,247,596 | 7/1941 | Boer | 209/130 |
| 3,059,772 | 10/1962 | Le Baron | 209/127 R |
| 3,114,877 | 12/1963 | Dunham | 324/71 CP |
| 3,244,279 | 4/1966 | Butler | 209/128 |
| 3,380,584 | 4/1968 | Fulwyler . | |
| 3,413,545 | 11/1968 | Whitby . | |
| 3,449,667 | 6/1969 | Gourdine | 324/71 CP |
| 3,462,609 | 8/1969 | Beattie . | |
| 3,561,253 | 2/1971 | Dorman . | |
| 3,710,933 | 1/1973 | Fulwyler et al. . | |
| 3,853,750 | 12/1974 | Volsy . | |

*Primary Examiner*—Joseph J. Rolla
*Attorney, Agent, or Firm*—William A. Newton

[57] ABSTRACT

Disclosed is a particle analyzer wherein uniformally charged liquid droplets, having a uniform velocity in a linear trajectory, proceed into a tubular electrode in which the electrostatic field is shaped to position particles on a center axis, and provide the particles with a rate movement along this axis that provides a sufficient time duration for evaporation of the droplets, the particles being subsequently deflected from said center axis or collected from said center axis, after evaporation.

50 Claims, 10 Drawing Figures

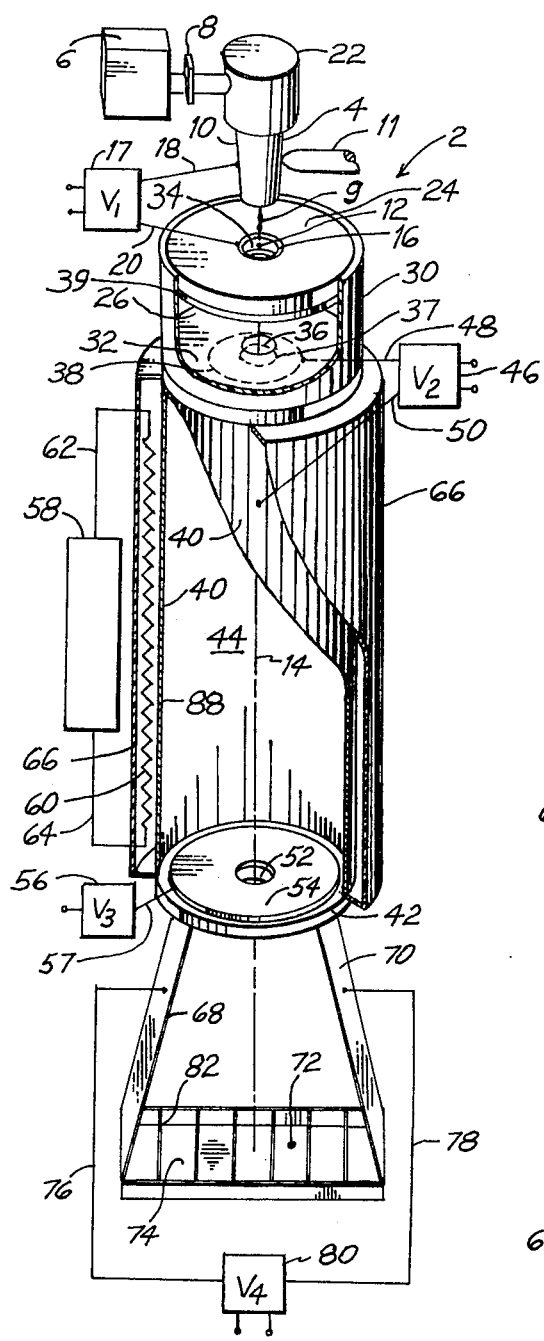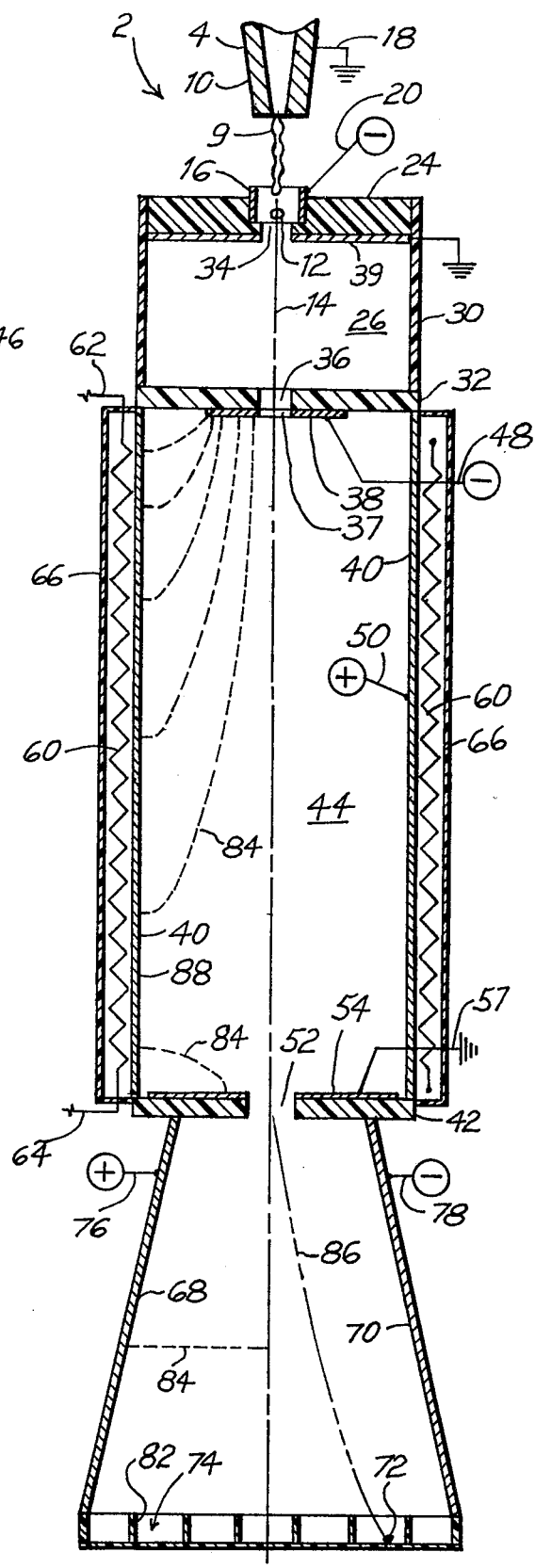
FIG. 1
FIG. 2

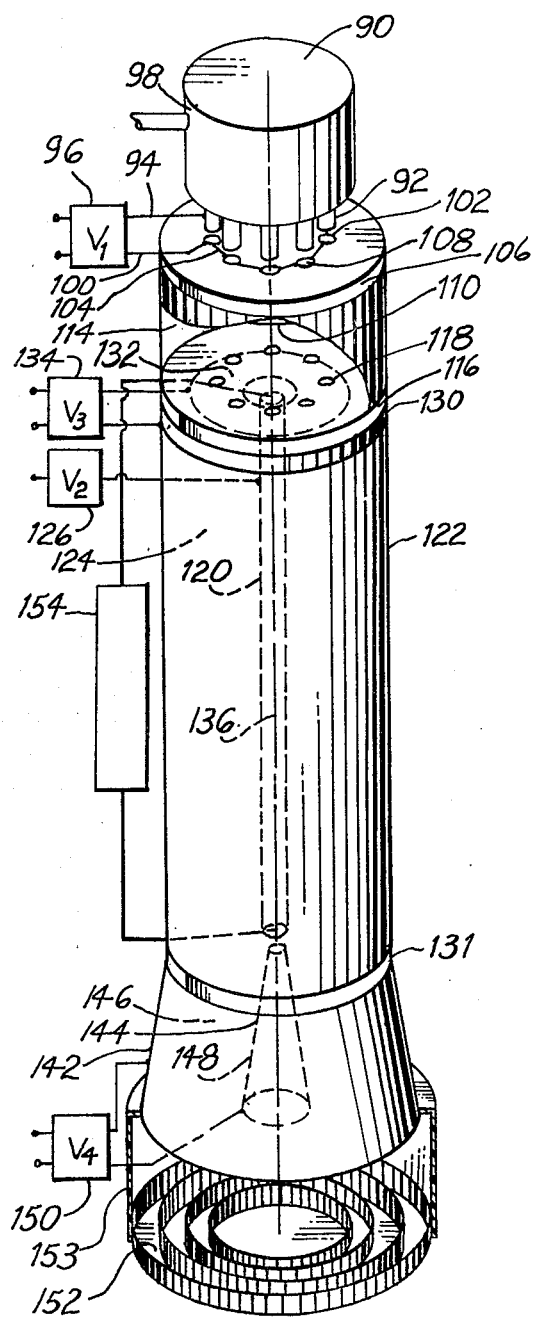
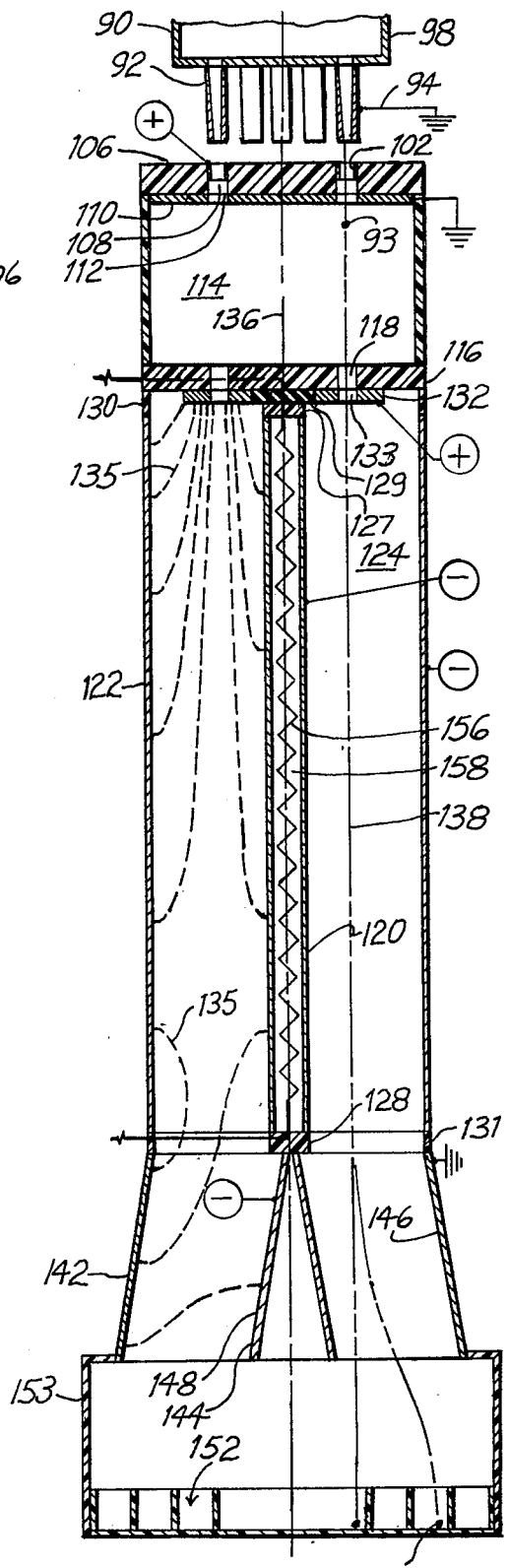
FIG. 3
FIG. 4

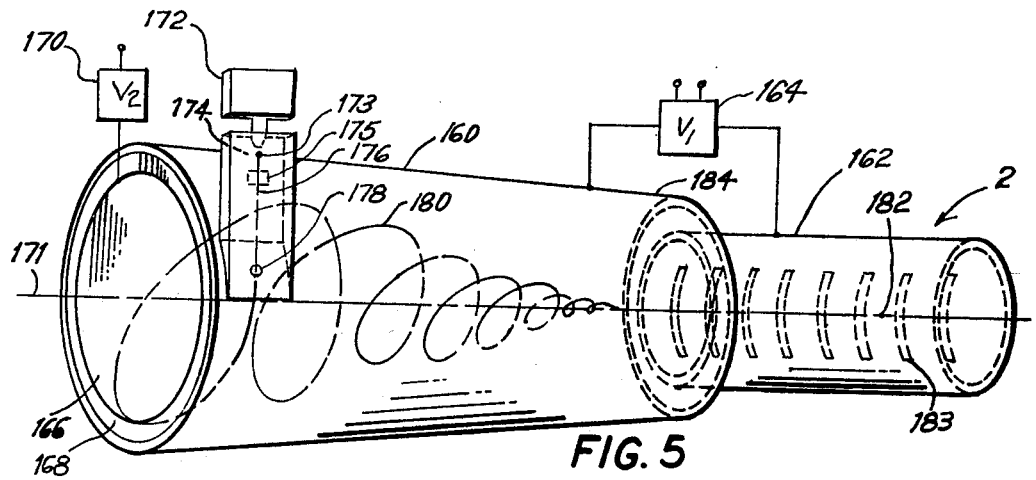
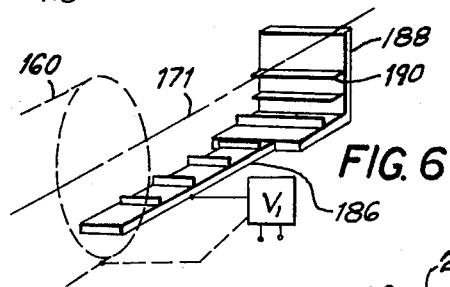
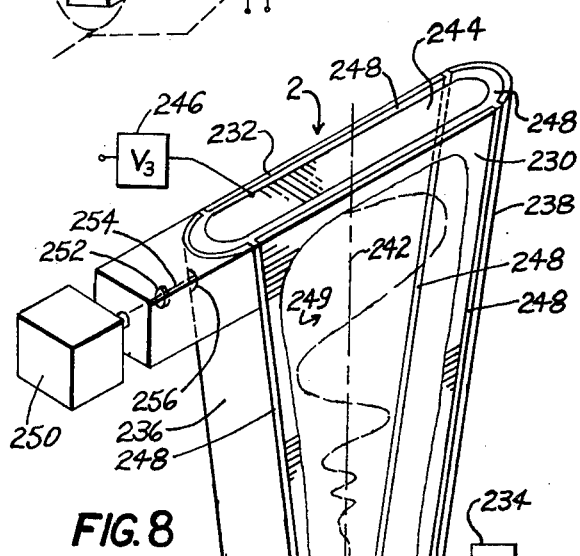
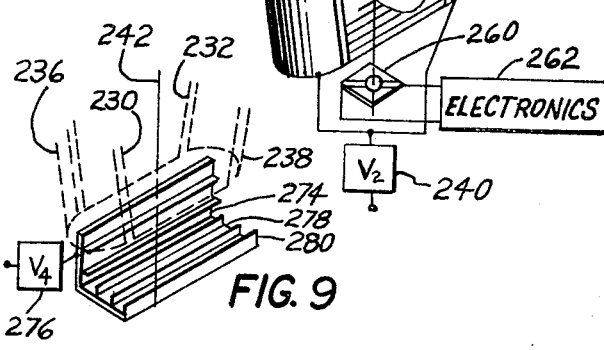
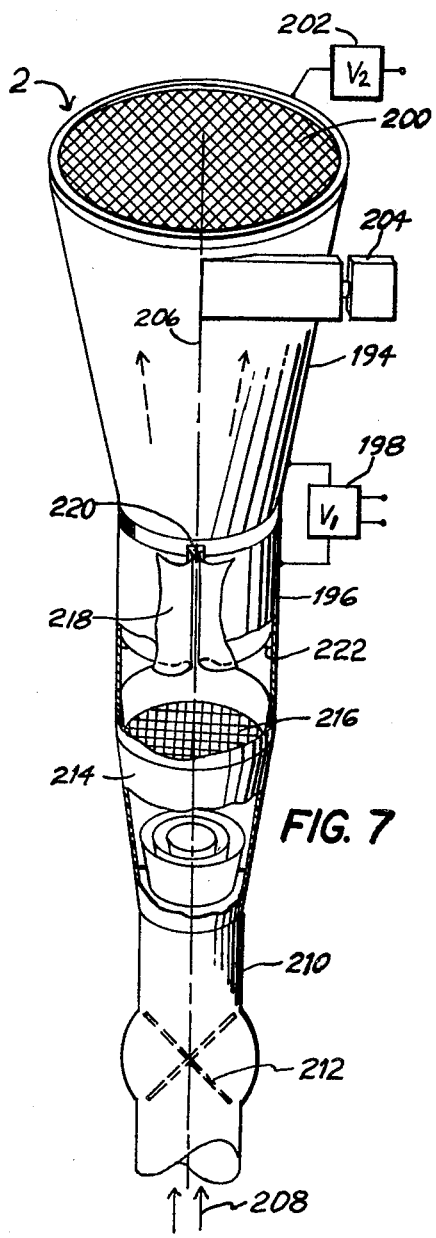

PARTICLE GUIDING APPARATUS AND METHOD

FIELD OF THE INVENTION

The present invention relates to the analysis of relatively small particles suspended in a liquid medium.

DESCRIPTION OF THE PRIOR ART

Primarily in the art of cytology, there exists automated particle analyzers wherein a liquid flow stream, having a suspension of individually isolated particles, is broken up into a plurality of uniform sized, equally charged droplets, as illustrated in U.S. Pat. No. 3,380,584 to Fulwyler and U.S. Pat. No. 3,710,933 Fulwyler et al. These charged droplets, which normally include no more than one particle, are analyzed according to measurable signals, such as stimulated fluorescent light, scattered light, light absorbance and electrical impedance, and then are sorted in an electrostatic field according to one or more of these signals. However, since each particle has a droplet of liquid encompassing it, analytical measurements commonly conducted on, for example, aerosols can not be undertaken. For instance, aerosols are frequently analyzed using electrostatic precipitation, with sorting of the particles being carried out according to their dimensions, as illustrated in U.S. Pat. No. 3,413,545 to Whitby and U.S. Pat. No. 3,853,750 to Volsy. In these prior art arrangements, an ionizer is normally used to discharge a stream of gas ions which are mixed with aersols' particles to impart thereto an electric charge. The charge acquired by the particles is proportional to the size of the particles. Hence, the electrical mobility of a given particle in an electrostatic field is related to particle size and particle charge. This electrical mobility has allowed the particles to be sorted by size and recent investigations, using electrometers and like probe devices, have correlated charge transfer to a probe from a particle as not only depending upon particle size, but also impact velocity and electrical resistivity of the particle material.

In the automated particle analyzers wherein droplets are formed, the size of the droplets normally range from 100 to 150 microns, with the particles therein normally ranging from 1 micron to 50 microns. Initial velocities of the droplets can be adjusted to typically range from 0.1 to 15 meters per second. Moreover, the density and size of the droplets will cause rapid acceleration of a droplet having an initially low velocity. On the other hand, the measurement of aerosol particle size distributions requires relatively small solid or liquid particles suspended in air or gas, such as smog, smoke, fog and mist. Generally, these particles, which typically range from 0.01 microns to 2 microns, do not appreciably settle at any significant rate in a gaseous medium at normal atmospheric pressure. Consequently, the prior art aerosol analyzer techniques have been limited to relatively small particles that can be suspended, at least temporarily, in a gaseous medium on a gas flow. Secondly, for particles to be analyzed by conventional aerosol techniques, they must not only be capable of suspension in a gas, but they must be capable of readily being separated into individually isolated particles. Hence, for example, biological cells, even if they were sufficiently small, could not be sufficiently separated and suspended in a gaseous medium in any substantial quantity. Moreover, the prior art aerosol analyzers have had very limited success in keeping the particles in a predetermined trajectory so as to allow accurate sorting. Typically, various gas flow sheath arrangements have been proposed. However, gas flows invariably have turbulance problems that lead to imprecise sorting results.

U.S. Pat. No. 3,561,253 to Dorman is of interest in that it discloses one of many probe like devices which use the impact of the particles thereon to determine the size distribution of the particles. U.S. Pat. No. 3,462,609 to Beattie discloses a nuclei counter for aerosols wherein an evaporation chamber is used.

Accordingly, it can be readily seen that there is a need for an apparatus and method of analyzing relatively large particles capable of being separated and suspended in a liquid, but not in a gaseous medium, without the particle being surrounded by the suspending liquid at the time of analysis.

SUMMARY OF THE INVENTION

The present invention is related to a particle guiding apparatus and method having droplet forming means for forming a plurality of uniformally charged, liquid droplets and for initially providing the droplets with a substantially uniform velocity in a substantially linear trajectory. Electrode means are provided for generating electrostatic forces for positioning the particles substantially along a center axis and for moving the particles along the center axis at a rate of movement to allow evaporation of the liquid of the droplets which encompasses the enclosed particle. The electrode means includes a tubular electrode, which is positioned to receive the droplets in its interior and is centered on the center axis, and a second electrode, which is positioned at one end of the tubular electrode. A potential difference is provided between the tubular and second electrodes so as to apply to the tubular electrode a charge of the same polarity as that of the droplets. After evaporation, the particles are sorted based upon their size and mass, or are collected on a probe for measurement of their charge transfer.

If the center axis is vertically aligned, the second electrode is positioned to shape the electrostatic forces to have a force component parallel to the center axis for initially retarding the particles downward movement along the center axis, thereby counteracting the gravitational force. For relatively small particles, a third electrode can be positioned at the other end of the tubular electrode to assist the particles' movement in the lower portion of the tubular electrode after evaporation is completed or nearly completed. If the center axis is horizontally aligned, then the second electrode is normally used to assist the movement of the particles, thereby overcoming air resistance. In either case, the tubular and second electrodes are aligned and configured for shaping the electrostatic field to provide an inwardly directed, radial force component for substantially aligning the particles with the center axis or a predetermined trajectory or plane from which they can be collected, or alternatively, deflected and then collected. If deflected, the amount of deflection is correlated with particle size and mass. In one embodiment, a counter flow of gas is used to suspend the particles in a tapered tubular electrode, with the field strength or gas flow being varied to suck out particles from the tubular electrode on a progressively increasing particle size basis. In another embodiment, the amount of gravitational settling, combined with particle velocities dependent upon size, allows for particle sorting. In another embodiment, deflection from a two dimensional plane is used for particle sorting. In the remaining embodiments, deflection from the center axis is the inherent sorting parameter. Depending upon the embodiments, the droplets are initially introduced along the center axis or substantially angled to the center axis, so as to take a looping orbit about the center axis to be reflected back and forth in a plane.

A subcombination of the particle guiding apparatus, comprising the tubular electrode and one or more other electrodes, has a variety of uses. This tubular electrode arrangement allows for the particles to be retained within a reasonably sized spacial region during which various acts may be performed on the droplets; whereby the gravitational force is a least partially compensated for. The tubular electrode arrangement provides for movement of the droplets through this spacial region at a reasonable speed so as to allow the particles to be subsequently processed or collected. The tubular electrode arrangement maintains the particles along a predetermined trajectory, or depending upon the embodiment, eventually centers the particles on the predetermined trajectory, and moves the droplets along the predetermined trajectory. This allows for ready collection and detection of particle characteristics or deflection of the droplets, which correlates with particle characteristics.

BRIEF DESCRIPTION OF THE DRAWINGS

Further objects and advantages of the present invention will become apparent as the following description proceeds, taken in conjunction with the accompanying drawings in which:

FIG. 1 is a side view of the first embodiment of the particle analyzer wherein the cylinder electrode 40, sidewall 30, and the housing 66 are partially broken away to show the interior.

FIG. 2 is a cross-sectional view of the first embodiment of FIG. 1.

FIG. 3 is a side view of the second embodiment of the particle analyzer wherein a portion of the structure is partially broken away to show the interior.

FIG. 4 is a cross-sectional view of the second embodiment of FIG. 3.

FIG. 5 is a side view of a third embodiment of the particle analyzer wherein some interior elements are shown by dashed lines.

FIG. 6 is a perspective view of a modification to the fourth embodiment of FIG. 5 wherein the annular electrode 160 is partially shown in a dashed outline.

FIG. 7 is a side view of a fourth embodiment of the particle analyzer wherein the cylinder electrode 196 and the expansion conduit 214 are partially broken away to show the interior.

FIG. 8 is a perspective view of a fifth embodiment of the particle analyzer wherein the tapered plate electrode 230 is partially broken away to show the interior.

FIG. 9 is a perspective view of a modification to the fifth embodiment of FIG. 8 wherein the electrodes 230, 232, 236 and 238 are shown in a dashed outline.

DETAILED DESCRIPTION OF THE PREFERRED EMBODIMENTS

Figure 10:
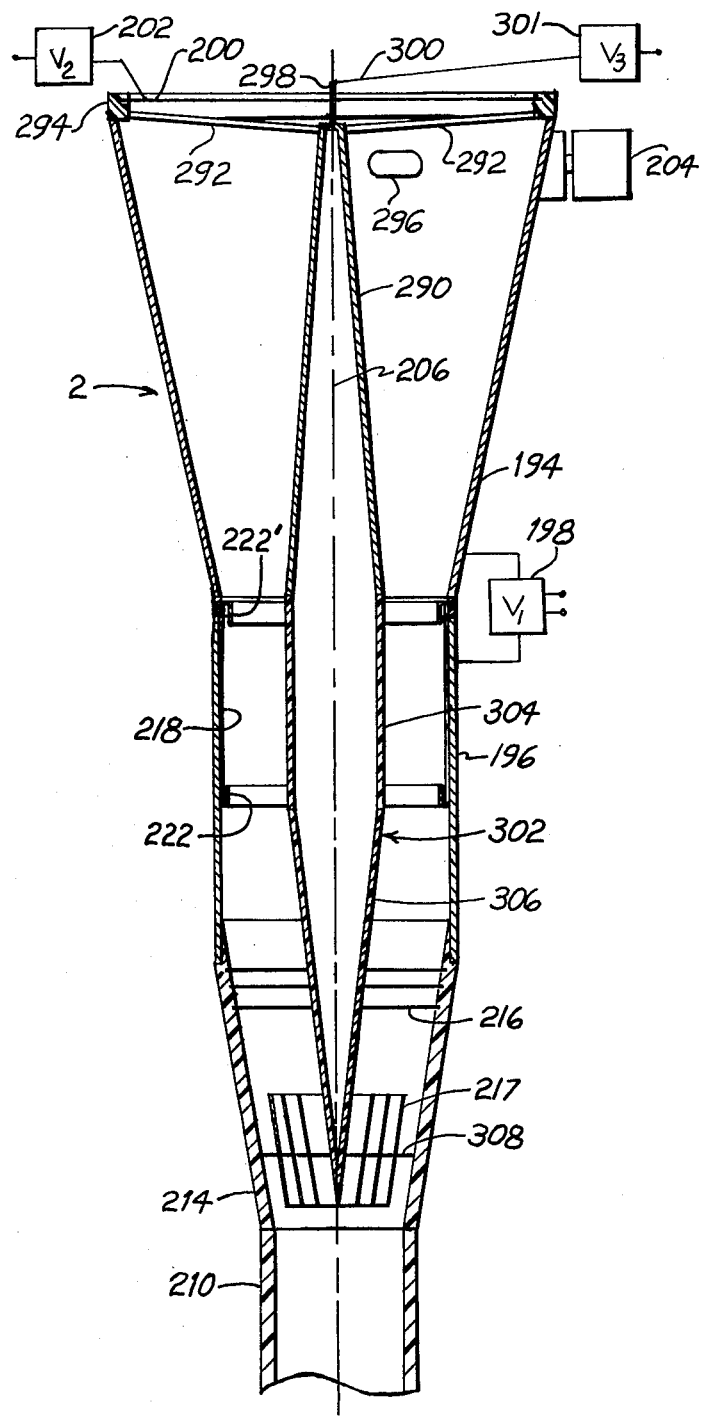
FIG. 10 is a cross-sectional view of a modification to the fourth embodiment of FIG. 7.

Referring to FIG. 1, there is disclosed a particle analyzer, which is generally indicated by numeral 2. The analyzer 2 includes a conventional droplet forming means 4, preferably of the type disclosed in U.S. Pat. No. 3,380,584 to Fulwyler and U.S. Pat. No. 3,710,933 to Fulwyler et al. As in these well known prior art arrangements, a dilute solution of particles is suspended in a liquid and feed from a fluid container 6, through a strainer 8, to the droplet forming means 4. The strainer 8 is employed to stop particles of a gross size from clogging the system, while allowing particles within a size range of interest to pass therethrough. In one implementation of the analyzer 2, biological cells are suspended in a highly volatile solvent, such as freon, having an ion producing solute, such as fluoroacetic acid. However, the analyzer 2 can be used with any granular material wherein the grains or particles can be separated and suspended in a liquid, for example by means of well known stirring methods. Moreover, although the suspending liquid is preferably highly volatile, less volatile liquids such as a saline solution or like aqueous solution, can be used, but their use results in slower throughput and, as will become apparent hereinafter, longer particle trajectories. As with these prior art arrangements, a flow stream, in the form of a liquid jet 9, is formed within a nozzle 10, and can include one or more liquid sheaths. In a well known manner, the nozzle 10 is coupled to vibration means (not shown) by means of a coupling rod 11. Vibrations imparted to the nozzle 10 produce minute disturbances or bunching on the liquid jet 9. By producing these disturbances at a proper frequency, determined by the diameter, viscosity and velocity of the jet 9, the bunching grows in size by surface tension, until the jet 10 is broken into evenly spaced, uniformly sized droplets 12. As is known in the art, the dilution of the particle sample introduced into the container 6, the size of the droplets 12, and the frequency of the ultrasonic mechanical disturbances conveyed by the coupling rod 11 are chosen so that, on a statistical basis, each droplet 12 normally contains no more than a single isolated particle, although some droplets 12 do not contain any particles. Typically, for particles having diameters from 1 to 50 microns, droplets 12 having diameters from 100 to 150 microns are desirable. Although the velocity of the jet 9 can be readily varied from 0.1 to 15 meters per second, due to the time required for hereinafter described operations, velocities toward the low end of this range are desirable. To those skilled in the art, it will be obvious that the above described set of conditions can be varied substantially, depending upon the intended usage of the analyzer 2. These droplets 12 have an initial linear trajectory along the center axis 14. Subsequently, the droplets 12 are charged by a conventional charging collar electrode 16, in the same manner as illustrated in the two above-mentioned patents. More specifically, a potential difference is applied between the nozzle 10 and the collar electrode 16 by a voltage source 17, by use of a pair of leads 18 and 20. Optionally, depending upon the use of the analyzer 2 of the invention, a conventional particle scanning means 22, as shown in the two above-mentioned patents, can be included for automatically analyzing the suspended particles in a conventional flow chamber (not shown) of the scanning means 22 to detect preselected physical or chemical characteristics of each particle by use of optical and/or impedance measurements. If particle analysis in the form of conventional optical measurements is desired, then the particle suspension liquid must be fairly transmissive to light. If particle analysis in the form of conventional impedance measurements is desired, then the particle suspension liquid must be reasonably conductive.

Referring to FIG. 1, there are two modes of operation of the charging collar electrode 16. In the first mode, all of the droplets 12 can be uniformly charged. In the first mode of operation, the particle scanning means 22 is not used. In other words, the collar electrode 16 is continuously at its charging voltage, without interruption. If the optical or impedance measurements are performed on the particles in the optional particle scanning means 22, in a second mode of operation the charging of a preselected subpopulation of particles can be accomplished in a manner illustrated in U.S. Pat. No. 3,710,933 to Fulwyler et al. This procedure charges only those droplets 12 containing particles of the preselected subpopulation.

As depicted in FIG. 1, the nozzle 10 is mounted on the center axis 14, preferably above a first circular panel 24. A first chamber 26 is defined by the first circular panel 24, a preferably cylindrical sidewall 30, and a second circular panel 32, each of which is in coaxial relationship with respect to each other along the center axis 14 and each of which is formed of a dielectric material. A first aperture 34, centered on the center axis 14, is formed in the first circular panel 24 and has the collar electrode 16 securely mounted therein. A second aperture 36, centered on the center axis 14, is formed in the second circular panel 32. A first ring plate electrode 38, having a circular perimeter and a circular center hole 37, is mounted on the underneath side of the second circular panel 32. Hence, the droplets 12 proceed from the nozzle 10, along the center axis 14, through the two apertures 34 and 36. The first chamber 26 provides a spaced-apart relationship between the collar electrode 16 and the first ring plate electrode 38. This spaced-apart relationship minimizes the influence of fringing from an electrostatic field, to be described hereinafter, on the collar electrode 16, the nozzle 10 and any optional impedance sensing occuring in the particle scanning means 22. Optionally, a grounded, metal disk 39, which acts as an electrostatic shield, can be used to minimize the desirable longitudinal length of the first chamber 26 along the center axis 14. The disk 39, which has a centered hole therein, is held at ground potential and is mounted on the underneath side of the first circular panel 24. The disk 39 can be modified to form an enclosure to surround and shield the nozzle 10 and the collar electrode 16 from the hereinafter described electrostatic field. The nozzle 10 and the collar electrode 16 have been exaggerated in size so as to more clearly show their detail.

As illustrated in FIG. 1, the second circular panel 32, a cylinder electrode 40, and a third circular panel 42 define a second chamber 44. The first ring plate electrode 38 and the cylinder electrode 40 are each formed of a conducting metal and are disposed in coaxial relationship with respect to each other along the central axis 14. A potential difference is impressed between the first ring plate electrode 38 and the cylindrical electrode 40 by a variable second voltage source 46 through a pair of leads 48 and 50. The first ring plate electrode 38 is charged with the opposite polarity to that of the droplets 12, while the cylinder 40 is charged with the same polarity as the droplets 12. The third circular panel 42 is formed of a dielectric material and has a third aperture 52 formed therein, and like the apertures 34 and 36, is axially centered on the center axis 14. Mounted on the top surface of the third circular panel 42 is a second ring plate electrode 54, which is formed of a conducting material and is axially centered about center axis 14. The electrode 54 is normally held at ground potential or a small potential of opposite polarity to that of the droplet 12 by a variable voltage source 56 through a lead 57. As will become apparent hereinafter in a detailed description of the first embodiment of the invention, the analyzer 2 is operable without the use of the second ring plate electrode 54 and the third circular panel 42, but their use is desirable. In the preferred implementation a heat input means 58 is shown having a radiation emitter in the form of a heating coil 60, disposed in spaced apart, adjacent relationship to the outside wall of the cylindrical electrode 40. Typically, the heat input means 58 would include a power source connected to the heating coil 60 through a pair of conductors 62 and 64. Although only one heating coil 60 is shown in FIG. 1, preferably a plurality of heating coils 60 are equally spaced about the exterior wall of the cylinder electrode 40 to heat the cylindrical shell 40 to desired temperature levels for rapid evaporation of the droplets 12. A cylindrical housing 66, formed of heat insulating material such as asbestos, is disposed in surrounding relationship to the heating coils 60 and the cylinder electrode 40. The heating coils 60 and insulated housing 66 are a conventional arrangement as shown by U.S. Pat. No. 3,462,609 to Beattie. Although the preferred embodiment contemplates a thermal energy transfer to the cylinder electrode 40 through heat radiation and convection, other means of heat transfer will be evident to those skilled in the art. Examples of other heat input means 58 which will, in view of the preferred embodiment, be obvious to those skilled in the art, are the use of infrared radiation and microwave radiation. However, in applications requiring the radiation emitter to be embedded in the cylinder electrode 40 or to extend into the second chamber 44, care must be taken to avoid any undue rearrangement of the desired electrostatic field, to be described hereinafter.

With reference to FIG. 1, positioned below the third circular panel 42, is a pair of oppositely charged deflector plates 68 and 70, which are disposed on opposite sides of the center axis 14 to deflect the particles 72 from their linear trajectories, along the center axis 14, into one of a plurality of particle collectors 74. The first deflector plate 68 and the second deflector plate 70 have a voltage difference impressed therebetween, through a pair of leads 76 and 78, by a variable fourth voltage source 80. Each of the particle collectors 74 comprise a region defined by adjacent dividers 82, with each divider 82 being preferably parallel to the lower edge of the deflector plates 68 and 70. Hence, with respect to the center axis 14, each successive particle collector 74 has a progressively increasing spacial displacement from the center axis 14. For the sake of clarity, a portion of the sidewall 30, the cylinder electrode 40 and the housing 66 have been broken away in FIG. 1 to illustrate the interior thereof.

The operation of the second chamber 44 of the first embodiment of the analyzer 2 can be better understood by reference to the enlarged cross-sectional view of FIG. 2. The droplets 12 proceed along the center axis 14, through the first chamber 26, into the second chamber 44. The influence of the hereinafter described electrostatic field on the velocity of the droplets 12 is minimal in the first chamber 26. Also, any such fringe field effects are radially symmetric about the center axis 14, so as not to effect the trajectories of the droplets 12.

Moreover, the relatively short distance of the first chamber 26, with respect to the center axis 14, minimizes increases in the velocities of droplets due to gravity. Hence, the droplets 12 enter the second chamber 44 so as to be substantially centered on the center axis 14 with velocities within a controllable range. For the purposes of illustration, it is assumed in the illustration of FIG. 2, that the polarities are such that a voltage of negative potential is applied to the collar electrode 16 and the nozzle 10 is grounded or negatively charged, so that a predetermined charge of positive polarity is applied to each droplet 12. Hence, as the droplets 12 pass into the second chamber 44, the droplets 12 are attracted to a negatively charged first ring plate electrode 38 and repelled by the positively charged cylinder electrode 40. More specifically, the electric field between the first ring plate electrode 38, the second ring plate electrode 54 and the cylinder electrode 40 is depicted on one side of the center axis 14 by force lines 84, which are shown in a simplified illustrative manner. The electrostatic field in the second chamber 44 is substantially radially symmetric with respect to the center axis 14. Moreover, the influence of the field in the second chamber 44 on the trajectory of a given particle 72 can be better visualized by looking at the parallel and perpendicular force components of the electrostatic field taken with respect to the center axis 14. As is well known, the field at any point, can be broken into perpendicular and parallel vector components exerted on a droplet 12 at a particular position. At the center axis 14 the perpendicular force component is essentially zero. At increasing radial displacements from the center axis 14 in a given plane perpendicular thereto, the perpendicular force component progressively increases. Hence, the perpendicular force component keeps the droplets 12 substantially centered on the center axis 14. With respect to movement of the droplets 12 and particles 72 along the center axis 14, the relative electrode voltages are preferably set so that the droplets 12 will experience a progressively weakening parallel force component. It is desired to counteract the gravitational force on the droplet 12 to the extent of minimizing or eliminating any downward acceleration of the droplets 12. Hence, at a given particle position, the parallel force component conteracts the gravitational force so as to retard the droplet's progress, in comparison to the droplet's projected progress through a gaseous medium not having the retarding electrostatic field arrangement. Hence, the respective voltages of the first ring plate electrode 38 and the cylinder electrode 40 are adjusted with respect to each other, so as to preferably generate a parallel force component which substantially counteracts the gravitational force as the particles enter the second chamber 44. During evaporation, the droplets 12, as they progress along the center axis 14, lose mass at a rate proportional to their surface areas. The droplets 12, and, as evaporation proceeds, just the particles, retain their charge during evaporation, without the escaping vapor removing the charge. In other words, the positive or negative ions, as the case may be, are not removed to any great extent by the escaping vapor. Also, as the droplets 12 move along the center axis 14, the droplets 12 experience an increasingly weakening parallel force component so as to compensate, to a considerable degree, for the decreasing weight of the droplets 12. Therefore, any tendency to substantially decrease or increase the velocity of the droplets 12, and eventually the particles 72, can be prevented, if desired. Moreover, some particularly small particles, for example 10 microns or less, frequently will become suspended or proceed too slowly in the gaseous medium, depending on the viscosity of the medium and the density of the particles. Therefore, the voltage on the second ring plate electrode 54 can be adjusted to provide an electrical attracting force for particles 72 in the lower portion of the second chamber 44. For example, with the illustrative set of conditions shown in FIG. 2, the droplets 12, and eventually just the particles 72, will experience a retarding, progressively decreasing parallel force component, which will become zero at a point substantially past the midpoint of the second chamber 44. After becoming zero, the parallel force component will reverse direction and start increasing in magnitude. Although the second ring plate electrode 54 is shown at ground potential, the potential is adjustable. Moreover, the polarities shown in FIG. 2 are merely illustrative and the magnitude of each voltage is adjustable. It is the relative differences in voltages of respective surfaces, with respect to the polarity of the charge on the droplets 12, that are the important trajectory influencing parameters. For example, if the droplets 12 were negatively charged, all the polarities would change. The respective voltages for given dimensions for the second chamber 44 can vary substantially, depending upon the size of the droplets 12, the velocity of the droplets 12, and the pressure and viscosity of the gaseous medium. Typically, the voltage difference between the first ring plate electrode 38 and the cylinder electrode 40 can, depending upon the above conditions, preferably range from a few 1000 volts up to 20,000 volts. In the preferred implementation, the gaseous medium is air at normal atmospheric pressure.

Referring to FIG. 2, the particles 72 approach the third aperture 52, with the surrounding liquid removed therefrom, in a linear trajectory along the center axis 14, with reasonable velocities. During evaporation, the particles 72 retain a relatively uniform charge with respect to each other. Those droplets 12, in the heretofore described second mode of operation, that are not charged, are either completely evaporated or pass on through without being deflected. Hence, the charged particles 72 will be deflected from their linear trajectories by a distance dependent upon the particles' velocity, cross-sectional area and mass. Lighter, smaller particles will land in more remotely disposed particle collectors 74 than heavier, larger particles. An illustrative trajectory 86 of a particle between plates 68 and 70 is shown in FIG. 2. Removal of the third circular panel 42 and the second ring plate electrode 54 results in a rearrangement of the electrostatic field so that some of the force lines terminate on one of the deflection plates 68 and 70. Although much less desirable, particle sorting can be accomplished with this modification.

With reference to FIGS. 1 and 2, the inner surface 88 of the cylinder electrode 40 has a circular cross-sectional configuration, and in the preferred embodiment, this circular cross-sectional configuration has the same radial displacement from the center axis 14 in all horizontally disposed planes, so as to produce the cylindrical configuration. However, it should be appreciated, that it is within the scope of the invention to have the radial displacement of the inner surface 88 vary, within reasonable limits, so long as the circular cross-sectional configuration is retained. Hence, the electrode 40, for example, could take on a truncated, hollow cone configuration. Such a cone configuration strengthens the electrostatic field in areas of smaller radii, with respect to areas of larger radii, and can be used to rearrange the rate of change of the parallel force component over that existing with the electrode 40 having a cylindrical configuration. As will be obvious to those skilled in the art, another way to accomplish this would be to divide the cylinder electrode 40 into a plurality of concentric portions, one on top of another and each being electrically insulated from the other. Hence, each successive concentric portion could be held at a different electrical potential, thereby rearranging the rate of change of the parallel force component exerted on the droplets 12 traveling down the center axis 14. Hence, for some intended uses, the rate of mass loss can be more closely correlated with the rate of the decrease in the parallel force component. In variations of the cylindrical electrode 40, the inner surface 88 thereof is definable as a surface of revolution. This surface of revolution comprises at least one curved or straight line, which is parallel or angled with respect to the center axis 14, revolved about the center axis 14. Each of the voltage sources 17, 46, 56, and 80 are D.C. voltage sources.

FIGS. 3 and 4 illustrate a second embodiment of the analyzer 2. Generally, the second embodiment is similar to the first embodiment, but provides a droplet forming means 90 with a plurality of nozzles 92, which allow for greater throughput of droplets 93. Each of the nozzles 92 is preferably held to ground potential by a conductor 94, which interconnects a variable D.C. first voltage source 96 with a metal casing 98 of the droplet forming means 90. A conductor 100 electrically couples the first voltage source 96 with a plurality of collar electrodes 102, each of which are electrically interconnected by connectors 104. If desired, each vertically aligned pair of nozzles 92 and collar electrodes 102 can charge droplets selectively by having a plurality of the previously described conventional particle scanning means, as shown with the first embodiment. In such a case, the collar electrodes 102 would not be electrically connected, but would be independently controlled. The plurality of nozzles 92 are equally spaced in a circular configuration. Hence, a first circular panel 106 has a plurality of first apertures 108 vertically aligned with the nozzles 92, each of the apertures 108 containing one of the collar electrodes 102. Mounted to the first circular panel 106 is an optional grounded disk 110, having a plurality of holes 112 vertically aligned with the first apertures 108. A first chamber 114 is formed between the first circular panel 106 and a second circular panel 116. The second circular panel 116 has a plurality of second apertures 118 vertically aligned with the first apertures 108. A conductive metal center post 120 is axially positioned inside of a cylinder electrode 122, with the cylinder electrode 122 defining a second chamber 124. Due to the small surface area of the center post 120, it preferably is held at a higher potential than the cylinder electrode 122, by a variable D.C. second voltage source 126. The polarity of the potential applied to the post 120 and electrode 122 is the same polarity as the charged droplets 93. Hence, the apertures 108 and 118 are radially aligned so that the particles enter into the electrostatic field at a point where the perpendicular force component is substantially zero. The center post 120 is mounted on opposed ends by plastic insulation blocks 127 and 128, and a rubber gasket 129. Plastic extension rings 130 and 131 are used to mount the cylinder electrode 122. In the second embodiment, a ring plate electrode 132 has a plurality of circular holes 133, with each of the holes 133 being positioned under one of the second apertures 118. A potential difference is impressed between the electrode 122 and the electrode 132 by a variable D.C. voltage source 134. A plurality of force lines 135 show, in a simplified illustrative manner, one possible electrostatic field configuration for a given set of voltage conditions. As with the first embodiment, the electrostatic field in the second chamber 124 is radially symmetric with respect to the center axis 136. In each plane perpendicular to the center axis 136, there is a circular region wherein the perpendicular force component is substantially zero. The apertures 108 and 118 are aligned on vertical axes which intercept this region. Hence, the droplets 93, as they proceed down the second chamber 124, will remain relatively centered in this region of zero perpendicular force components, as shown by a sample trajectory 138. Although the trajectory 138 is shown as a straight line, it can be curved. The important fact is that the particles 140 approach the end of the second chamber 124 along trajectories having the same radial profile. As with the first embodiment, the parallel force component on a given droplet 93, that retards the droplet's 93 progress, decreases in strength as the droplet 93 proceeds down the second chamber 124 of the second embodiment, until the parallel force component becomes zero, if desired. Likewise, if desired, the respective voltages can be adjusted so that, for very small particles 72, the parallel force component on the particle 72 reverses direction so as to stop retarding, and starting attracting the particle 140, after most of the surrounding liquid or all of the surrounding liquid has been removed.

With reference to FIGS. 3 and 4, a conductive outer deflector electrode 142 and a conductive inner deflector electrode 144 are concentrically centered on the center axis 136. Both deflector electrodes 142 and 144 are formed of metal, have circular cross sections and are preferably tapered outward toward their bottoms, although they could assume other radially symmetrical shapes, such as a cylinder. The primary feature of the deflector electrodes 142 and 144 is that they have an inner surface 146 and an outer surface 148, respectively, that are surfaces of revolution, formed by a straight or curved line, which is angled or parallel to the center axis, with the line being revolved about the center axis 136. In the preferred implementation, the deflector electrodes 146 and 148 have the configuration of truncated, hollow cones. A variable D.C. voltage source 150 is used to adjust the voltages of the deflector electrodes 144 and 146 so that the outer deflector electrode 142 is grounded or is oppositely charged with respect to the cylinder electrode 122 and the center post 120, whereby a portion of the force lines 135 therefrom terminate on the outer deflector electrode 142. The second embodiment is operable without the use of the deflection electrode 144. If desired, the electrode 144 can be included in strengthening the outwardly directed radial force component used for deflecting the particles. In FIG. 4 a set of polarities are assigned to each conductive surface merely for the purposes of illustrating the operation of the second embodiment of the analyzer 2. However, it is the relative differences in the voltages of respective conducting surfaces, with respect to the polarity of the charged droplet 12, which are the factors that effect the droplet trajectories. As the particles 140 approach the deflector electrodes 142 and 144, and enter the region therebetween, the droplets encounter an outwardly directed, radially aligned perpendicular force component. Hence, the charged particles 140 are deflected into particle collectors 152 according to their cross-sectional area, velocity and mass. Heat input means 154 is shown having a heating coil 156 positioned inside a hollow portion 158 of the center post 120. However, as in the first embodiment, it could be positioned on the outside of the cylinder electrode 122. A housing 153, formed of a non-conducting material, is disclosed around the concentric collectors 152.

With reference to both embodiments of FIGS. 1 through 4, according to Stokes law, larger sized particles will be slowed more by the gaseous medium. Also, larger masses have greater inertia. However, with normal atmospheric pressure, variations in size, which induce variations in velocities, are the dominate sorting parameter for the small size particles under consideration. The droplets, through evaporation, will lose mass, and therefore size, at approximately the same rate during the first portion of their travel through the second chamber 44 or 124. Also, the droplets are initially uniform in size. Consequently, the air resistance and velocities of the droplets at a given vertical position in the second chamber will not substantially vary between the droplets, during this first portion of their travel. Without the use of the retarding electrostatic field, the droplets would, during this first portion of their travel, accelerate to excessive velocities, despite air resistance. As the droplets lose mass and, at a lesser rate, size, the air resistance becomes more effective in retarding the droplets progress, hence the retarding electrostatic field is tailored to become progressively weaker. Hence, as previously described, any variations in velocities during this first portion of travel can be kept relatively small, and if there are variations in velocities, velocities will be substantially uniformly the same between droplets at a fixed position. As the evaporation process reaches the particles, thereby causing the evaporation to slow or stop for those particles, variations in velocities between particles will occur, since particles at a given position no longer have the same size. Therefore, during the second portion of the particles' travel, which includes at least a substantial portion of travel where the electrostatic field can be an attracting force, smaller sized particles will acquire slower velocities than larger particles. As the particles pass between the deflector electrodes, a third portion of their travel, particles with slower velocities will be acted upon by the perpendicular force component for a longer time period. Hence, variations in velocities will tend to deflect smaller particles by greater radial displacements. Moreover, acting to enhance this effect is the fact that air resistance will impede the radial velocity component of larger particles to a greater degree. Therefore, smaller particles will be deflected more than larger particles so as to allow sorting on this basis.

The first and second embodiments of the particle analyzer 2 utilize the electrostatic field to keep the droplets in relatively linear trajectories, and to retard the droplets' progress, thereby retaining them in a predetermined region of the second chamber 44 or 124 for a sufficient length of time to allow completion of the desired evaporation. The embodiments to be described hereinafter permit the droplets to spin or reflect within a predetermined region. Hence, a greater throughput can be achieved, since the droplets can have higher initial velocities than in the previously described embodiments.

A third embodiment of the particle analyzer 2 is shown in a top view in FIG. 5. A conductive annular electrode 160, preferably having a truncated cone configuration, and a downstream cylinder electrode 162 have a potential difference impressed therebetween by a first variable D.C. voltage source 164. The annular electrode 160 is charged with a voltage of the same polarity sign with respect to that of the charge on the droplets. The cylinder electrode 162 is charged with a voltage having the opposite polarity sign as the particles, or if desired, is held at ground potential. An optional circular plate electrode 166 is positioned at the end of the annular electrode 160 and is separated therefrom by a non-conducting material 168. The circular plate 166 is charged by a second variable D.C. voltage source 170. Consequently, as with the previous described embodiments, the electrostatic field is substantially radially symmetric with respect to a center axis 171. As with the previously described embodiments, the strength and configuration of the electrostatic field can be varied by changing the respective voltages of the various electrodes.

With reference to FIG. 5, a droplet forming means 172 is positioned so that droplets 173, which are formed in a first chamber 174 with a charging collar electrode 175, proceed in a linear trajectory 176 and pass through an aperture 178, which is formed in the annular electrode 160. The linear trajectory 178 is orientated so as to be preferably tangent to the inner surface of the annular electrode 160, but spaced apart therefrom. Although only one droplet forming means 172 is shown, a plurality of the droplet forming means 172 can be cooperatively positioned about the end of the annular electrode 160. The droplets will be continuously deflected from the annular electrode 160 so as to spin in a looping manner, as shown by an illustrative looped trajectory 180. Movement along the center axis 171 can be assisted or retarded, depending upon the polarity and magnitude of the voltage applied to the circular plate electrode 166. Also, the linear trajectory 176 can be slightly angled with respect to the plane of the drawing to assist or retard the rate of droplet progression along the center axis 171. If the circular plate electrode 166 is grounded or held to a potential opposite in sign to that of the droplets, the inward, radially directed electrostatic force component of the electrostatic field at the adjacent end of the annular electrode 160 will be strengthened so as to deflect droplets of greater velocities and/or size. This is due to some of the adjacent force lines from the annular electrode 160 terminating on the circular plate 166, therefore increasing the charge density at the adjacent end of the annular electrode 160. To overcome the parallel electrostatic force component, which initially attracts the particles to the circular plate 166, it is necessary to angle the droplet forming means 172 so that the linear trajectory 176 has a forward velocity component, parallel to the center axis 171 and in the direction of the cylinder electrode 162. Consequently, the respective voltages and the angle of linear trajectory 176 can be adjusted to account for droplet size and droplet velocity. As with the previously described embodiments, the perpendicular force component of the electrostatic field, which is directed radially inward toward the center axis 171, is essentially zero along the center axis 171, both within the annular electrode 160 and the cylinder electrode 162. Gravitational settling has only a minimal initial influence on the looped trajectories 180, when the droplets are heavier. As the droplets lose their initial velocity, through the friction of the air and their mass, through evaporation, the perpendicular force component of the field will center the droplets and particles substantially on the center axis 171. Heavier particles can settle below the center axis 171, due to their weight, but in general while the particles are in the annular electrode 160, effects of the gravitational force are minimal. The particles 182, under the influence of an increasing parallel electrostatic force component, will be accelerated along the center axis 171. The smaller particles, in accordance with Stokes Law, acquire greater velocities. In the cylinder electrode 162, the perpendicular electrostatic force component on a given particle is now directed outward in a radial manner. Hence, as the gravitational force settles the particles slightly, with the heavier particles descending first, a given particle proceeds from a region of essentially zero perpendicular force component, to a region of downward directed perpendicular force components, so as to acquire a migration velocity toward the cylinder electrode 162. Hence, heavier particles take a curved downward trajectory earlier, in the stronger portion of the field. Additionally, the larger particles will have slower velocities, both perpendicular and parallel to the center axis 171. The interior of the cylinder electrode 162 is subdivided into a plurality of collectors by dividers 183. If the particles adhere to the surface, as is usually the case, the dividers 183 are not necessary, except for the purpose of facilitating measurement. Therefore, the heavier, larger particles will be precipitated between nearer dividers 183, while the lighter, smaller particles will be progressively precipitated between more remote dividers 183. The heat input means has its heating coils, along with its outside housing, disposed around the outside of the annular electrode 160, but is not shown in this embodiment for the sake of better illustrating the remaining structure. Also, electrostatic shielding, as with the other embodiments, can provide for shielding the droplet forming means 172 and the collar electrode 175. Increasing the tapering of the annular electrode 160 so as to have a smaller diameter neck 184, better centers the particles, but at the same time it slightly weakens the field strength at the opposed end. As previously mentioned, this weakening of the field can be strengthened by having some of the force lines from the annular electrode 160 to terminate on the circular plate electrode 166. Although the third embodiment is positioned so that the center axis 171 is horizontally disposed, it will become apparent hereinafter that the entire structure can be rotated so that the center axis 171 is vertically disposed and with some modifications, be operable.

With reference to FIG. 5, the droplet forming means 172 could be aligned to introduce the particles along the center axis 171 at the end of the annular electrode 160, in a manner similar to that illustrated in FIG. 1. Depending upon the velocity and initial weight of the droplets, this modification can make the circular plate electrode 166 unnecessary. Hence, the initial centering of the droplets along the center axis 171 results in the droplets moving substantially along center axis 171, or slightly below due to gravitational settling through the entire annular electrode 160. In this contemplated modification, if the droplets' velocities are substantial, or if additional strength is needed for the perpendicular force component at the end of the annular electrode adjacent to the droplet forming means 172, due to heavy droplets, then the circular plate electrode 166 can be retained, with a droplet receiving aperture being formed therein. In this case, the annular electrode 160 would provide an attractive force for the droplets which would, first, reduce the forward velocity of the droplets, therefore minimizing the required length of the annular electrode 160. Secondly, heavy droplets would be positioned closer to the center axis 171, due to the increased charge density at that end of the annular electrode; hence, heavier particles can be processed. Likewise, this same modification can be accomplished by removing the third circular panel 42, the second ring plate electrode 54, and the deflector plate 68 from the first embodiment of FIGS. 1 and 2. When the particle analyzer 2 is rotated so that the center axis 14 is horizontally disposed, the particles can be collected on the remaining deflector plate 70, with the landing spot on the deflector plate 70 being dependent upon particle weight and size. When the droplets are introduced into the annular electrode 160 with relatively low initial velocities, this arrangement is desirable in that it allows for slow longitudinal movement for the particles during evaporation, while permitting accelerated particle velocities during deflection and sorting of the same. On the other hand, if the droplets are initially introduced into the cylinder electrode 162 along the center axis 171, with the circular plate electrode 166 being removed, high velocities are required to get the particles through the annular electrode 160, and are therefore normally undesirable, since insufficient time is provided for evaporation.

FIG. 6 illustrates a modification to the third embodiment of FIG. 5, wherein a conductive flat plate electrode 186, perferably having a retangular shape, is substituted for the cylinder electrode 162 of FIG. 5. An L-shaped end portion 188, formed of nonconducting material, is mounted at the end of the flat plate electrode 186. A plurality of parallel dividers 190, formed of nonconducting material, are mounted in protruding relationship along the interior walls of the flat plate electrode 186 and the end portion 188. The end of the annular electrode 160, with the center axis 171, is shown in a broken line outline. Preferably, the flat plate electrode 186 is disposed in a horizontal plane. With this modification, the force lines of the electrostatic field become progressively less radially symmetric about the center axis 171 as they approach the flat plate electrode 186, with most of the force lines bending downward sharply to the flat plate electrode 186. The distance traveled by a given particle down the center axis 171 will be effected by the particle velocity with respect to the center axis 171, which is dependent upon particle size and mass; and the downward migration velocity, which is dependent upon particle size. Hence, larger and heavier particles travel a shorter distance along the center axis 171, and land between nearer dividers 190. Most types of particles sorted will adhere to the surface upon which they impinge. The particle analyzer 2 of FIG. 5, as modified in FIG. 6, can be rotated so that the center axis 171 is vertically disposed. In such a case, the circular plate electrode 166 must be oppositely charged with respect to the particles, so as to provide an attractive force to counteract the gravitational force. This has the advantage of strengthening the inwardly directed, radial force exerted by the electrostatic field on the particles in the upper part of the annular electrode 160.

FIG. 7 shows a fourth embodiment of the particle analyzer 2. The fourth embodiment is the structure of the third embodiment of FIG. 5, modified to include a gas flow, so that for any given particle, the electrostatic force can be balanced against the force of the gas flow. The particle analyzer 2 includes an annular electrode 194 and a cylinder electrode 196, having a voltage difference impressed therebetween by a variable D.C. first voltage source 198. A circular electrode 200 is charged by a variable D.C. second voltage source 202. Particles are formed by one or more droplet forming means 204. This portion of the structure is the same as that shown in FIG. 5. A center axis 206 is vertically orientated. A gas flow, indicated by direction arrows 208, is introduced by a tubular conduit 210. The tubular conduit 210, having a circular cross-sectional configuration, has a fan 212 mounted therein. The tubular conduit 210 is coupled to an expansion conduit 214, which has a truncated cone configuration and acts as an expansion chamber for the incoming gas flow. A nylon diffusion screen 216 is positioned in traversing relationship to the air flow to insure a laminar flow. Although only one screen 216 is shown for simplicity, a number of screens 216 are positioned in gas flow traversing relationship in the expansion conduit 214. The cylinder electrode 196 is partially broken away to shown the diffusion screen 216. A plurality of concentric, truncated cone shaped guide vanes 217, formed of a nonconducting material, are positioned downstream with respect to the nylon screens 216, to assure good gas flow conditions. It is desirable to have the gas flow as strong or stronger about its periphery, as compared to its center, while the gas flow proceeds through the cylinder electrode 196. This prevents the gas flow from disrupting the electrostatic centering of the particles at the end of the annular electrode 194. In other words, the particles will not be dispersed radially outward by the gas flow, prior to the particles reaching the cylinder electrode 196. The circular electrode 200 is formed of a metal grid, which allows the gas flow to pass therethrough. If desired, the tubular conduit 210 can be coupled to the end of the annular electrode 194, with a fine particle filter incorporated therein, so as to form a closed recirculating system.

With reference to FIG. 7, the gas flow generally decreases in velocity in direct proportion to the square of the increasing diameter of the annular electrode 194. Hence, the air velocity decreases with upward vertical movement in the annular electrode 194. The droplets are introduced in a tangential manner so that they loop about, until they sufficiently lose their initial velocity. Initially, the large, heavy droplets will have a downward gravitation force, which is proportional to the cube of their diameter, and upward force exerted by the gas flow, which is proportional to the square of their diameter. At a given vertical height in the annular electrode 194, as the droplets lose mass, the gravitational force decreases at a faster rate than the force of the gas flow. However, in actuality, the droplets will be descending in the annular electrode 194, which means that for a given droplet, the velocity of the retarding gas pressure, on a per unit of area basis, will be increasing and also, the velocity accelerating electrostatic force component, parallel to the center axis 206, will be increasing. The circular electrode 200 is held at a voltage to either repel or attract the droplets in the upper portion of the annular electrode 194, as needed. With a predetermined degree of tapering of the annular electrode 194, the respective voltages and the gas flow can be appropriately set so that a batch of droplets can be suspended in the annular electrode 194. Then the voltage applied to the cylinder electrode 196 can be gradually increased, or alternatively, the gas flow rate can be decreased. Smaller particles, having less air resistance, will slowly enter into the inner region of the cylinder electrode 196. Since the region of zero perpendicular electrostatic force component is so small within the region, the particles will almost immediately proceed, in one direction or another, to the cylinder electrode 196 and be collected. Preferably, but not necessarily, a flexible, thin plastic tape 218 can be mounted to slidingly pass along the interior surface of the cylinder electrode 196. To accomplish this, a relatively narrow vertical slit 220 is formed in the cylinder electrode 196 to allow the tape 218 to be fed from a first spool (not shown) and back out to a second spool (not shown). For the purposes of clarity, the tape 218 is shown as being broken off and the cylinder electrode 196 is shown broken away so as to show the bottom portion of the tape 218. The tape 218 is mounted inside the cylinder electrode 196 by two spaced apart, circular groove tracks 222 (partially shown), which hold the upper and lower edges of the tape 218 for sliding engagement against the inside of the wall of the cylinder electrode 196. As the particles proceed toward the cylinder electrode 196, they impinge upon and adhere to the tape 218. Depending upon the type of particle collected, the tape 218 can have a sticky, exposed surface to insure the adherence of the particles.

Referring to FIG. 7, the voltage can be progressively increased on the cylinder electrode 196, or alternatively the gas flow can be progressively decreased, so that progressively larger particles will proceed into the cylinder electrode 196 and be collected on the tape 218. Since the tape 218 is continuously moving, each time there is a change in voltage or gas flow, an indicia mark can be made on the tape 218. Hence, there will be groupings of similar size particles between indicia marks. Alternatively, the particle analyzer 2 can be rotated so that the center axis 206 is horizontally disposed, thereby allowing the system to operate similar to the embodiment of FIG. 5. In such a case, the gas flow can be used to only slightly retard the forward progress of the droplets. Heat input means, which surrounds the annular electrode 194, is not shown, since it is the same as shown with the previously described first embodiment.

A fifth embodiment of the particle analyzer 2 is illustrated in FIG. 8. This embodiment is, in a sense, merely a modification of the embodiment of FIG. 5. In FIG. 5, the droplets, during evaporation, are contained within a volume having a cone-like configuration. In the embodiment of FIG. 8, the droplets could better be described as being contained within a plane, as will become apparent as the description proceeds. The particle analyzer 2 has a pair of parallel, opposed, tapered plate electrodes 230 and 232, formed of metal which preferably have the configuration of an equal sided trapezoid, or to describe it another way, a truncated equilateral triangle. The tapered plate electrodes 230 are relatively closely spaced together and are charged at the same voltage, which has the same polarity as that of the droplets by a variable D.C. first voltage source 234. A pair of opposed, curved electrodes 236 and 238, formed of metal and preferably having a semi-circular cross section, are positioned along the lateral sides of the electrodes 230 and 232. The curved electrodes 236 and 238 are charged with the same voltage, having the same polarity as that of the droplets, by a variable D.C. second voltage source 240. A center axis 242 is defined to be equally spaced from each opposed pair of electrodes. A metal top plate electrode 244 is horizontally positioned along the top of the four previously described electrodes. The top plate electrode 244 is held to a voltage opposite in polarity to that of the charge on the droplets, or held to ground potential, by a variable D.C. third voltage source 246. All five electrodes are separated from each other at their adjacent edges by insulating material 248. A droplet forming means 250, in association with a charging collar electrode 252, projects droplets along an intially horizontal linear trajectory 254, so that the droplets enter the region between the five electrodes through an aperture 256. Most of the force lines from the electrodes 230, 232, 236 and 238 terminate on the top plate electrode 244, with there being, for a given droplet or particle, a region of essentially zero perpendicular electrostatic force component along the center axis 242. In other words, a droplet, and eventually just the particle therein, when positioned on the center axis 242, will experience only an upward directed electrostatic force component which is parallel to the center axis 242, with the perpendicular force component being zero. This parallel force component along the center axis 242 decreases in magnitude with increasing displacement from the top plate electrode 244. As the droplets or particles deviate from the center axis 242, they experience a perpendicular force component that progressively increases in magnitude. Hence, the droplets, while evaporating, will bounce back and forth between the two curved electrodes 236 and 238 until their initial velocities have been dampered out sufficiently to allow the droplets and particles to be centered on the center axis 242, with downward directed velocities. The electrostatic field not only centers the droplets and particles, but it also retards their downward progress, and therefore counteracts the gravitational force, for a sufficient length of time to allow evaporation. For very light particles, it is necessary to include a horizontally disposed bottom plate electrode (not shown) along the bottom of the electrodes 230, 232, 236 and 238, with an aperture formed therein for the particles to pass therethrough, similar to the second ring plate electrode 54 of the first embodiment of FIGS. 1 and 2. This is due to particularily small particles becoming suspended in the air, or actually proceeding back to the top plate electrode 244. As with the second ring electrode plate 54 of FIG. 1, this bottom plate electrode exerts only an attractive parallel force component on particles centered on the center axis. It is also contemplated that the gas pressure and viscosity could be decreased to avoid particle suspension, if desired. In summary, the fifth embodiment is shown without the bottom plate electrode to show the operation of this embodiment with larger sized particles, in excess of 10 microns in diameter. Also, this embodiment illustrates that nonradially symmetric electrostatic fields can be used in some situations. Heat input means (not shown) would have its heating coils disposed in adjacent, spaced apart relationship to the outside walls of the tapered plate electrodes 230 and 232. The heat input means and its surrounding housing, as shown in FIGS. 1 and 2, is not included in FIG. 8 so as to better show the electrode structure. Although separate electrodes 230, 232, 236 and 238 are used, these electrodes could be electrically coupled to form one single electrode. In such a case, there would only be a potential difference impressed between the top plate electrode 244 and the combined electrode. However, it is desirable to have two pairs of opposed electrodes, so that the voltage on the curved electrodes 236 and 238 can be higher than on the tapered electrodes 230 and 232. In any case, the electrodes define an elongated tubular electrode arrangement 249 with planar sides parallel to an elongated axis, which is perpendicular to the center axis 242. The elongated tubular electrode arrangement can have, as explained, one or more electrode elements. The curved electrodes 236 and 238 can assume other shapes, such as being flat, but the curved configuration is preferable because it tends to minimize particle deviations to regions of weaker electrostatic forces found in right angle corners of electrodes. Hence, particle deviation out of its plane, when approaching the curved electrodes 236 and 238, is minimized. The tapered electrode 230 is cut away in FIG. 8 to show the interior of the tubular electrode arrangement 249.

Referring to FIG. 8, the fifth embodiment also represents a variation that can be readily included in all the embodiments, except the embodiment illustrated in FIG. 7. Heretofore, electrostatic precipitation of particles, based upon their size and mass, was implemented upon a stream of centered particles proceeding in the same direction. However, other processes can be performed on this stream of particles, as will be obvious to those skilled in the art. For instance, in FIG. 8 a particle detector 260 with its associated electronics 262, is positioned on the center axis 242 to intercept the particles. The particle detector 260 and its electronics 262 are of conventional design and are used to measure particulate mass or charge transfer. There are numerous types of particle detectors known, such as that illustrated in U.S. Pat. No. 3,561,253 to Dorman and U.S. Pat. No. 3,413,545 to Whitby.

FIG. 9 illustrates a variation to the fifth embodiment shown in FIG. 8. The particle detector 260 of FIG. 8 is replaced with an electrostatic precipitator arrangement comprising a rectangular shaped plate electrode 274, held to a voltage opposite in polarity of the charged particles, or at ground potential, by a variable D.C. fourth voltage source 276. Attached at right angles to the bottom of the rectangular electrode 274 is a panel 278, formed of nonconductive material. A plurality of parallel, spaced apart dividers 280, formed of a nonconducting material, are mounted on the adjacent walls of the rectangular electrode 274 and the panel 278. In operation, the electrostatic force lineson the lower portion of the electrodes 230, 232, 236 and 238 will terminate on the rectangular electrode 274. Hence, the attraction of the rectangular electrode 274 causes varying amounts of deviation for the particles; and therefore determines which dividers 280 they land between. This arrangement has one other unique feature. Even though the particles have not stopped reflecting back and forth is essentially a plane, which is parallel to the electrodes 230 and 232 and passes through the center axis 242, they can be fairly accurately reflected out of the plane by the rectangular electrode 274. The particle velocity component parallel to the center axis 242, which it acquires as it proceeds downward, is primarily a function of the particles' size, and does not significantly vary as the velocity component perpendicular to the center axis 242 oscillates back and forth, reversing direction upon each reflection. Both velocity components lie within the heretofore described plane. As the particles leave the surrounding electrodes 230, 232, 236 and 238, they generally proceed off in an angled direction with respect to the center axis, if they have a residual perpendicular velocity component. However, the duration of the deflecting influence of the rectangular electrode 274 is a function of the parallel velocity component, not the perpendicular velocity component, since the particle is essentially being deflected out of the plane. Increasing displacement from the plane determines between which dividers 280 the particles will land.

FIG. 10 shows a modification to the embodiment of FIG. 7. A cone-shaped electrode 290 is co-axially mounted along the center axis 206 inside of the annular electrode 194 by means of a plurality of support bars 292, which are composed of a non-conducting material. The support bars 292 are secured to a mounting rim 294, formed of electrical insulating material and used to support the circular electrode 200. As in FIG. 5, the droplets proceed from the droplet forming means 204 through an elongated aperture 296 formed in the annular electrode 194. A non-conducting conduit member 298 protrudes upward from the electrode 290 through the circular electrode 200 and allows for an electrical lead 300 to pass therethrough and to electrically connect with the electrode 290. At the other end, the lead 300 connects with a third variable D.C. voltage source 301. The electrode 290, like electrode 194, is held at a voltage which has the same sign as the charge applied to the droplets. The electrode 290 is attached at its lower end to an air flow guide 302, formed of non-conducting material, such as plastic. The air flow guide 302 has an upper cylindrical portion 304 and a lower cone-shaped portion 306. A plurality of thin, rod-like brackets 308, which are used to mount the guide vanes 217, are used to support the lower end of the cone-shaped portion 306. The centers of the nylon screens 216 are removed to allow the cone-shaped portion 306 to pass therethrough. The tracks 222 and 222', with the tape 218 retained therein, are clearly shown in this figure.

Referring to FIG. 10, in operation, when the droplets are introduced along an initially horizontal trajectory into the annular electrode 194, the droplets, which are repulsed by both the annular electrode 194 and the cone-like electrode 290, will orbit in a helical path about the electrode 290, until they become stationary at some elevation. In other respects, this embodiment operates in a similar manner to that of FIG. 5. The inclusion of the electrode 290 gives a larger increasing gradient for the air resistance with respect to movement of the droplets in a downward direction. The air flow guide 302 maintains laminar air flow conditions. It is also contemplated that droplets could be introduced through the circular electrode 200 with a vertical disposed initial trajectory and sorted by the distance they travel with respect to the center axis 206 before being deposited, as shown by their vertical landing spot on the tape 218, or if no tape 218, on the cylinder electrode 196. The imposition of the electrode 290 can provide all the particles with the substantially same radial displacement as they leave the annular electrode 194. No suspension of the particles is achieved in this implementation and it's very similar to the embodiment of FIGS. 3 and 4, except a gas flow is included.

Referring to FIG. 10 in particular and to all the FIGURES in general, as with all the embodiments of this application, two different voltage source arrangements are shown. For example, the voltage source 301 is shown with a single lead, which signifies that it is providing a single voltage or potential with respect to the electrical ground. The other arrangement, such as the voltage source 198, is shown, as having two leads and providing two potentials or voltages to two electrodes, or to put it another way, providing a potential difference for the two electrodes. However, each of these dual voltage sources could have been shown by two separate single voltage sources. Each electrode surface is held to a given voltage or potential to create the desired potential differences between respective surfaces so as to achieve the desired electrostatic field shaping. Each voltage source includes a potentiometer or like means for each voltage supplied so that each voltage to each electrode is adjustable to its desired level with respect to electrical ground.

In summary, each of the embodiments define a tubular electrode which is centered on the center axis, from which the particles will be subsequently deflected. The tubular electrode comprises the cylinder electrode 40 in FIGS. 1 and 2, the cylinder electrode 122 in FIGS. 3 and 4, the annular electrode 160 in FIGS. 5 and 6, the annular electrode 194 in FIG. 7, and the elongated tubular arrangement 249 in FIG. 8, which can have one or more electrode elements. In each arrangement, there is a second electrode to which most of the force lines from the tubular electrode terminate. In embodiments where the center axis is substantially vertically disposed, the second electrode can be near the droplet forming means to retard the droplets' progress, as with the first ring plate electrode 38 in FIGS. 1 and 2, the ring plate electrode 132 in FIGS. 3 and 4, and the top plate electrode 244 in FIG. 8. In embodiments where the center axis is substantially horizontally disposed, the second electrode is normally positioned at the end of the tubular electrode opposite to the droplet forming means to attract the particles through the tubular electrode, as illustrated by the cylinder electrode 162 in FIG. 5 and the flat plate electrode 186 in FIG. 6. Alternatively, the second electrode can be used to counteract a gas flow, as illustrated by the cylinder electrode 196 in FIG. 7. Moreover, a third electrode is included in some embodiments to assist or counteract the effects of the second electrode at the opposite end of the tubular electrode from the second electrode. Examples of this are the second charged ring electrode 54 in FIGS. 1 and 2; the outer deflector electrode 142 in FIGS. 3 and 4, which also cause particle deviation; the circular plate electrode 166 in FIG. 5; the circular electrode 200 in FIG. 7; and the plate electrode 274 in FIG. 9 which also causes particle deviation. If either the second or third electrode is not used for particle deviation, then added deflector electrodes are needed, such as deflector plate 68 and 70 in FIGS. 1 and 2.

The embodiments of the particle analyzer 2 can be used for a variety of purposes, with a few illustrative purposes being discussed hereinafter. Biological cells can be diluted in a water insoluble, highly volatile liquid in container 6, with the volatile liquid being evaporated off, without significantly evaporating the less volatile water content of the cells. Hence, the cells can be electrostatically precipitated according to their actual size and weight. Alternatively, the cells could be impacted upon a probe to correlate charge transfer with particle size, impact velocity and electrical resistivity. Secondly, the water content of the cell can be removed and replaced with a highly volatile liquid, such as freon, by a known process of substituting alcohol and then freon, since alcohol is soluble in both water and freon. Hence the freon of the droplet and the freon contents of the cell can be evaporated, leaving a dried cell to sort. In general, numerous granular substances, which cannot be readily suspended in air, can be suspended in a liquid, and then processed according to the present invention. This would include particles that can not be readily separated from each other, but can be separated from each other when placed in a liquid, and, for example, stirred. Also, this would include particles that settle too rapidly to allow suspension of the particles in a gaseous medium for a sufficient length of time to allow sorting, without the use of turbulant gas flows. It is also contemplated that uniformally charged particles of a given size will impact into a given collector with the same impact velocity. Hence, it may be possible to correlate charge transfer with the particle's electrical resistance, since other charge transferring factors are the same. The particles to be analyzed can be solid or liquid. For instance, the solution in container 6 can comprise a solvent having a vapor pressure greater than the vapor pressure of a solute. If the vapor pressure of the solute is sufficiently low, the solvent will be evaporated, leaving the solute as particles for subsequent deflection.

The particle analyzer 2 can be used to maintain the droplets in a limited spacial region for performing acts on the droplets or particles, other than evaporation. Moreover, the analyzer 2 can process droplets which do not decrease in size and weight. For instance, constant sized droplets can be sorted based upon the charge applied thereto, or based upon the charge remaining on the droplet. The deflector electrodes 142 and 144 in FIGS. 3 and 4 can be used by themselves, without the electrodes 120 and 122, where the droplets do not need to be retained in a spacial area, but just need to be sorted, based on, for example, the applied charge. Also, droplets can be introduced in gross, such as in a spray, charged by an ionizer, and then centered and sorted by the tubular electrode arrangement. The charge acquired by ionization will primarily depend upon the droplets size, as shown by said U.S. Pat. No. 3,413,545, and will allow the droplets to be eventually centered and moved along a predetermined trajectory, even though the droplets are not initially introduced in a linear trajectory with a predetermined direction. More specifically, the droplet formation with individually isolated particles therein is particularly useful when combined with the tubular electrode arrangements heretofor described. However, it is contemplated that it will be obvious to those skilled in the art to apply the tubular electrode arrangement of the invention to a wide range of uses. Such uses may include liquid droplets that may or may not have particles therein, that may or may not remain in a liquid state and that may or may not retain its liquid, size and mass. With much lower throughput, and longer processing times, the droplets can be introduced into the tubular member in a random manner, such as by a conventional spray arrangement. In general, the tubular electrode arrangements disclosed herein provide means for maintaining the droplets along a predetermined trajectory, or at least eventually centering the droplets thereon, thereby allowing for any droplet manipulation requiring the consistent alignment of substantially all of the droplets, such as sorting the droplets. Likewise, the effects of gravity and air resistance on small droplets are overcome, so as to allow the droplets to be acted upon or manipulated within a reasonable spacial region, such as occurs when the liquid from the droplets is evaporated. Likewise, the tubular member provides means for moving the droplets through this spacial region for subsequent processing, such as occurs when at least one characteristic of the particle is detected. Given this flexibility of the electrode arrangements, many variations to the acts performed upon the droplets, either while in the tubular electrode or after having passed therethrough, are possible and are within the scope of this invention.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. In a particle analyzer including droplet forming means for forming a plurality of liquid droplets, having individually isolated particles contained therein, and for initially providing the droplets with a substantially uniform velocity in a substantially linear trajectory, and means for charging the droplets, the improvement comprising:

evaporating means for evaporating the liquid of of the droplets which surrounds the particle therein;

electrode means for generating an electrostatic field for positioning the particles substantially along a center axis and for moving the particles along said center axis at a sufficient rate of movement to allow completion of the evaporation of the droplets within a predetermined region;

detection means for measuring the particle's characteristics after completion of the evaporation of the droplets.

2. The particle analyzer of claim 1 wherein said detection means comprises means for electrostatic precipitation of the particles based upon the particle's characteristics.

3. The particle analyzer of claim 1 wherein said detection means comprises a particle detector for determining particle mass.

4. The particle analyzer of claim 1 wherein said evaporating means includes heat input means for increasing the rate of evaporation of the droplets.

5. The particle analyzer of claim 1 wherein said center axis is substantially vertically disposed, said electrode means includes retarding means for shaping the electrostatic field to have a force component parallel to said center axis for initially retarding the particle's downward movement with respect to the center axis, whereby the particle's velocities are retarded while they are heavy.

6. The particle analyzer of claim 5 wherein said electrode means includes accelerating means for shaping the electrostatic field to have a force component parallel to said center axis for assisting the particle's downward movement with respect to the center axis after the particle's movement has been retarded by said retarding means, whereby the particle's velocity is increased after it has been reduced in weight through evaporation.

7. The particle analyzer of claim 6 wherein said electrode means includes centering means for shaping the electrostatic field to have an inwardly directed, radial force component for centering the droplets on said center axis.

8. The particle analyzer of claim 1 wherein said center axis is substantially horizontally disposed, said electrode means includes acceleration means for shaping the electrostatic field to have a force component parallel to said center axis for forward movement of the particles with respect to the center axis.

9. The particle analyzer of claim 8 wherein said acceleration means provides a force component of progressively increasing magnitude with increasing particle displacement along said center axis.

10. The particle analyzer of claim 9 wherein said electrode means includes centering means for shaping the electrostatic field to have an inwardly directed, radial force component for centering the droplets on said center axis.

11. The particle analyzer of claim 1 wherein said electrode means comprises,
a tubular electrode having said center axis as its longitudinal axis, said tubular electrode being adapted to receive the droplets from the droplet forming means;
a second electrode being positioned substantially at one end of said tubular electrode;
means for impressing a potential difference between said tubular electrode and said second electrode to apply a charge of the same polarity as the charged droplets to said tubular electrode and a charge of the opposite polarity to said second electrode, whereby said tubular electrode exerts a repelling force and said second electrode ererts an attractive force on the particles.

12. The particle analyzer of claim 11 wherein said tubular electrode has an inner surface with a circular cross section; said second electrode comprises a first ring electrode disposed in surrounding relationship to said center axis at an end of the tubular electrode which is adjacent the droplet forming means, the droplet forming means being positioned so that the initial linear trajectory of the droplets is substantially colinear with said center axis, whereby said droplets proceed through the center of the first ring electrode and into an electrostatic field which is substantially radially symmetric about said center axis.

13. The particle analyzer of claim 12 further comprising,
a second ring electrode being disposed in surrounding relationship to said center axis at the end of said tubular electrode which is opposed to the end adjacent to said first ring electrode;
means for providing a potential difference between said tubular electrode and said second ring electrode to apply a charge to said second ring electrode of opposite polarity to that of the charged droplets; whereby the particles are retarded while being large and heavy, but are accelerated along said center axis after becoming small and light.

14. The particle analyzer of claim 13 wherein said detection means comprises a pair of oppositely charged deflector plates disposed to deflect the particles from said center axis, whereby the amount of deflection can be correlated with particle size.

15. The particle analyzer of claim 11 wherein said tubular electrode has an inner surface with a circular cross section; said second electrode comprises a circular plate electrode centered on said center axis at an end of the tubular electrode which is adjacent the droplet forming means; further comprising,
a center post electrode, having a circular cross section, which is axially positioned inside said tubular electrode along said center axis, said droplet forming means being positioned to introduce the droplets into the region between said tubular electrode and said center post electrode;
means for providing a potential difference between said center post electrode and said circular plate electrode to apply to said center post electrode a charge of the same polarity as the droplets.

16. The particle analyzer of claim 15 wherein said droplet forming means includes a plurality of nozzles disposed in a circle about said center axis.

17. The particle analyzer of claim 15 wherein said circular plate electrode has a plurality of holes formed therein, with each said hole being vertically aligned with one of said nozzles.

18. The particle analyzer of claim 15 wherein said detection means includes a first deflector electrode, having a circular cross-sectional configuration, which is centered on said center axis below said tubular electrode, means for providing a potential difference between said tubular electrode and said first deflector electrode to apply to said first deflector plate a charge of opposite polarity to the charged droplets.

19. The particle analyzer of claim 18 wherein said detection means further includes a second deflector electrode having a circular cross-sectional configuration and being interiorly disposed in coaxial relationship to the oppositely charged said first deflector electrode.

20. The particle analyzer of claim 18 wherein said detection means further includes a plurality of concentric collectors centered on said center axis.

21. The particle analyzer of claim 11 wherein said tubular electrode has an inner surface with a circular cross-sectional configuration; said droplet forming means being orientated to have its linear trajectory disposed to be substantially tangential to said inner surface, whereby the particles follow a looping trajectory until their initial velocities are dampered out.

22. The particle analyzer of claim 21 wherein said second electrode has a circular cross-sectional configuration and is disposed in coaxial relationship to said tubular member at the end of said tubular member which is oppositely disposed to the droplet forming means, said center axis being substantially horizontally disposed, whereby the particles will be precipitated inside of said second electrode.

23. The particle analyzer of claim 21 wherein said tubular electrode terminates in a circular electrode held at a potential independent of the potential applied to said tubular electrode and said second electrode.

24. The particle analyzer of claim 21 wherein said second electrode comprises an electrode positioned on one side of the center axis at the end of said tubular member which is oppositely disposed to the droplet forming means.

25. The particle analyzer of claim 11, wherein said tubular electrode and said second electrode each have a circular cross-sectional configuration and are disposed in coaxial relationship to each other, further including:
means for introducing a gas flow through said second electrode into said tubular electrode.

26. The particle analyzer of claim 25, wherein said tubular electrode has a progressively increasing diameter with respect to displacement along said center axis in a direction away from said second electrode.

27. The particle analyzer of claim 26, further including:
a circular electrode formed of a metal grid positioned adjacent the end of the tubular electrode opposite the second electrode, means for providing a potential difference between said tubular electrode and said circular electrode to apply a charge to said circular electrode of opposite polarity to the droplets.

28. The particle analyzer of claim 27, wherein said center axis is vertically disposed.

29. The particle analyzer of claim 11 wherein said tubular electrode has a cross-sectional configuration having an elongated axis which is perpendicular to said center axis, said tubular electrode including a pair of opposed planar electrode portions which are disposed in equally spaced relationship from said center axis and said elongated axis and further including a pair of opposed end electrode portions which are disposed in equally spaced relationship from said center axis and are centered on said elongated axis, the droplet forming means being orientated so that its linear trajectory is angled with respect to the center axis, but substantially passing through and being parallel to a plane formed by said elongated axis and said center axis.

30. The particle analyzer of claim 29, wherein said end electrode portions have inward facing concave surfaces.

31. The particle analyzer of claim 29, wherein said center axis is substantially vertically disposed, said second electrode comprises a top plate electrode disposed in perpendicular relationship to said center axis at the top of said tubular electrode.

32. The particle analyzer of claim 29, wherein said second electrode is positioned adjacent the end of the tubular electrode which is oppositely disposed to the droplet forming means.

33. The particle analyzer of claim 29, wherein said planar electrode portions are electrically insulated from said end electrode portions, means for separately charging said planar electrode portions and said end electrode portions.

34. A guiding apparatus for controlling the velocities and paths of droplets, that are at least initially liquid, comprising:
means for forming a plurality of liquid droplets from a sample liquid;
means for charging the droplets;
at least one tubular electrode;
means for introducing the charged droplets into the interior of said tubular electrode at a position substantially at one end of said tubular electrode;
a second electrode being positioned substantially at one end of said tubular electrode;
means for impressing a potential difference between said tubular electrode and said second electrode to apply a charge of the same polarity as the charged droplets to said tubular electrode and a charge of opposite polarity to said second electrode;
whereby the droplets are centered, at least eventually, on a predetermined trajectory passing through said tubular electrode and are moved along the predetermined trajectory at controlled velocities to provide time for individual processing of each droplet.

35. The guiding apparatus of claim 34, wherein said sample liquid comprises a relatively volatile carrier liquid and a relatively non-volatile substance contained therein, further comprising:
evaporating means for removing said carrier liquid of said droplets to leave said non-volatile substance, essentially prior to the droplets exiting from said tubular electrode.

36. The guiding apparatus of claim 34, wherein said tubular electrode has a center axis, said tubular electrode being substantially equally spaced from said center axis in any line passing perpendicular through said center axis.

37. The guiding apparatus of claim 36,
said center axis being substantially vertically aligned;
said second electrode being disposed adjacent the upper end portion of said tubular electrode;
said means for introducing the droplets being positioned at the upper end portion of said tubular electrode;
whereby the electrostatic field of said electrodes at least partially counteracts the gravitational force on the droplets.

38. The guiding apparatus of claim 36,
said center axis being substantially horizontally aligned;
said second electrode being positioned adjacent one end portion of said tubular electrode and said means for introducing the droplets being positioned at the other end portion of said tubular electrode;
whereby the electrostatic field of said electrodes assists in moving the particles along the predetermined trajectory.

39. The guiding apparatus of claim 36 wherein said tubular electrode has an inner surface with a circular cross section; said second electrode comprises a first ring electrode disposed in surrounding relationship to said center axis at an end of the tubular electrode which is adjacent the droplet forming means, the droplet forming means being positioned so that the initial linear trajectory of the droplets is substantially colinear with said center axis, whereby said droplets proceed through the center of the first ring electrode and into an electrostatic field which is substantially radially symmetric about said center axis.

40. The guiding apparatus of claim 39 further comprising,
a second ring electrode being disposed in surrounding relationship to said center axis at the end of said tubular electrode which is opposed to the end adjacent to said first ring electrode;
means for providing a potential difference between said tubular electrode and said second ring electrode to apply a charge to said second ring electrode of opposite polarity to that of the charged droplets.

41. The guiding apparatus of claim 40 further including having a pair of oppositely charged deflector plates disposed to deflect the particles from said center axis, whereby the amount of deflection can be correlated with the amount of particle charge.

42. The guiding apparatus of claim 36 wherein said tubular electrode has an inner surface with a circular cross section; said second electrode comprises a circular plate electrode centered on said center axis at an end of the tubular electrode which is adjacent the droplet forming means; further comprising,
a center post electrode, having a circular cross section, which is axially positioned inside said tubular electrode along said center axis, said droplet forming means being positioned to introduce the droplets into the region between said tubular electrode and said center post electrode;
means for providing a potential difference between said center post electrode and said circular plate electrode to apply to said center post electrode a charge of the same polarity as the droplets.

43. The guiding apparatus of claim 42 wherein said droplet forming means includes a plurality of nozzles disposed in a circle about said center axis, said circular plate electrode has a plurality of holes formed therein, with each said hole being vertically aligned with one of said nozzles.

44. The guiding apparatus of claim 42 further including a first deflector electrode, having a circular cross-sectional configuration, which is centered on said center axis below said tubular electrode, means for providing a potential difference between said tubular electrode and said first deflector electrode to apply to said first deflector plate a charge of opposite polarity to the charged droplets.

45. The guiding apparatus of claim 36 wherein said tubular electrode has an inner surface with a circular cross-sectional configuration; said droplet forming means being orientated to have its linear trajectory disposed to be substantially tangential to said inner surface, whereby the particles follow a looping trajectory until their initial velocities are dampered out.

46. The guiding apparatus of claim 36, wherein said tubular electrode and said second electrode each have a circular cross-sectional configuration and are disposed in coaxial relationship to each other, said droplet forming means and said second electrode being substantially disposed at opposed ends of said tubular electrode, further including:
    means for introducing a gas flow through said second electrode into said tubular electrode.

47. The guiding apparatus of claim 46, wherein said tubular electrode has a progressively increasing diameter with respect to displacement along said center axis in a direction away from said second electrode, said center axis is vertically disposed; further comprising
    a circular electrode formed of a metal grid positioned adjacent the end of the tubular electrode opposite the second electrode, means for providing a potential difference between said tubular electrode and said circular electrode to apply a charge to said circular electrode of opposite polarity to the droplets.

48. The guiding apparatus of claim 36 wherein said tubular electrode has a cross-sectional configuration having an elongated axis which is perpendicular to said center axis, said tubular electrode including a pair of opposed planar electrode portions which are disposed in equally spaced relationship from said center axis and said elongated axis and further including a pair of opposed end electrode portions which are disposed in equally spaced relationship from said center axis and are centered on said elongated axis, the droplet forming means being oriented so that its linear trajectory is angled with respect to the center axis, but substantially passing through and being parallel to a plane formed by said elongated axis and said center axis.

49. A method of separating a relatively volatile liquid from a relatively non-volatile substance, said method comprising the steps of:
    forming a plurality of liquid droplets from the volatile liquid containing the non-volatile substance;
    charging the droplets;
    removing the volatile liquid from the droplets by evaporation in a predetermined region;
    guiding the droplets along a predetermined path passing through the predetermined region by shaping an electrostatic field to have an inwardly directed, radial force component for centering the droplets on the predetermined path;
    moving the droplets along the predetermined path at controlled velocities to allow for completion of the evaporation of the droplets within the predetermined region by further shaping the electrostatic field to have a force component parallel to said predetermined path that approximately varies in strength to coordinate with the changing size and mass of the droplet so as to minimize velocity changes of the droplets.

50. The method of claim 49, further comprising the step of,
    detecting the characteristics of the non-volatile substance after the volatile liquid has been removed therefrom.

* * * * *